United States Patent

Jautelat et al.

[11] 4,399,309
[45] Aug. 16, 1983

[54] PREPARATION OF 1-ARYLOXY-METHYL KETONES

[75] Inventors: Manfred Jautelat, Burscheid; Jörg Stetter, Wuppertal; Dieter Arlt, Cologne, all of Fed. Rep. of Germany

[73] Assignee: Bayer Aktiengesellschaft, Leverkusen, Fed. Rep. of Germany

[21] Appl. No.: 335,942

[22] Filed: Dec. 30, 1981

[30] Foreign Application Priority Data

Jan. 16, 1981 [DE] Fed. Rep. of Germany ....... 3101143

[51] Int. Cl.³ .............................................. C07C 45/51
[52] U.S. Cl. ..................................... 568/322; 568/306
[58] Field of Search ................................ 568/322, 306

[56] References Cited

U.S. PATENT DOCUMENTS 3,920,668 11/1975 Nickl et al. ........................ 568/322
3,975,446 8/1976 Kitogaki et al. .................... 568/322

OTHER PUBLICATIONS

Bulletin de la Societe Chimique de France, C. Rivalle et al., 1972, pp. 2749-2755.
Tetrahedron Letters No. 22, 1943-1946-1978, Stephen F. Martin and Ta-shue Chou.

Primary Examiner—James H. Reamer
Attorney, Agent, or Firm—Sprung, Horn, Kramer & Woods

[57] ABSTRACT

A process for the preparation of a 1-aryloxy-methyl ketone of the formula

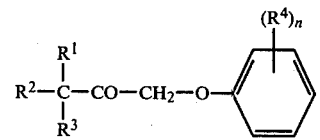

in which
$R^1$, $R^2$ and $R^3$ each independently is hydrogen, optionally substituted alkyl, alkenyl, alkynyl or optionally substituted aryl, or
$R^1$ and $R^2$ together are an alkylene chain,
$R^4$ each independently is halogen, alkyl, alkoxy, optionally substituted aryl or nitro, and
n is 0, 1, 2 or 3, comprising hydrolyzing a 1-halogeno-2-aryloxy-1-alkene of the formula

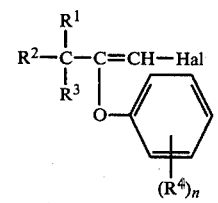

in which Hal is chlorine or bromine,
under acidic conditions at a temperature from about 20° to 150° C. until it is about 95 to 100% complete, adding a base, and then bringing the reaction to completion under weakly alkaline conditions at about 20° to 150° C. Advantageously all stages of the reaction are effected in a single vessel at a temperature from about 40° to 100° C. and in the presence of an inert organic solvent, optionally in admixture with water as a solution or as a two-phase system, about 1 mol of a monobasic acid and 2 mols of alkali metal carbonate being employed per mol of the 1-halogeno-2-aryloxy-1-alkene. The end products are known intermediates for fungicides.

10 Claims, No Drawings

PREPARATION OF 1-ARYLOXY-METHYL KETONES

The present invention relates to an unobvious process for the preparation of certain 1-aryloxy-methyl ketones, some of which are known and which can be used as intermediate products for the synthesis of fungicidally active compounds.

It is known that monohalogenomethyl ketones can be reacted with phenols in the presence of suitable bases to give 1-aryloxy-methyl ketones (in this context, see, for example, DE-AS (German Published Specification) No. 2,201,063 (Le A 14 118) and DE-AS (German Published Specification) No. 2,401,715 (Le A 15 410)). The monohalogenomethyl ketones required therefor can be prepared by halogenation of methyl ketones (see, for example, Houben-Weyl, "Methoden der Organischen Chemie" ("Methods of Organic Chemistry"), Volume 7/2 c, page 2162, Georg Thieme Verlag, Stuttgart (1977)). This process has the disadvantage that the halogenation and the reaction with phenols are carried out in two separate steps.

The present invention now provides a process for the preparation of a 1-aryloxy-methyl ketone of the general formula

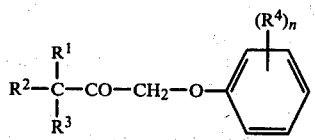

in which
$R^1$, $R^2$ and $R^3$ are selected independently and each represent hydrogen, optionally substituted alkyl, alkenyl, alkynyl or optionally substituted aryl, or
$R^1$ and $R^2$ together can represent an alkylene chain,
$R^4$ represents halogen, alkyl, alkoxy, optionally substituted aryl or nitro and
n represents 0, 1, 2 or 3, the substituents $R^4$ being selected independently when n is 2 or 3,
in which a 1-halogeno-2-aryloxy-1-alkene of the general formula

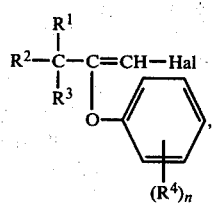

in which
Hal represents chlorine or bromine and
$R^1$, $R^2$, $R^3$, $R^4$ and n have the abovementioned meanings,
is subjected to acid hydrolysis in the temperature range of between +20° and 150° C. until it is about 95 to 100% complete and, after a basic substance has been added, the reaction is brought to completion under weakly alkaline conditions in the aforesaid temperature range.

The abovementioned known conversion of monohalogenomethyl ketones into 1-aryloxy-methyl ketones is carried out in anhydrous solvents. It is therefore exceptionally surprising that 1-aryloxymethyl ketones can also be obtained in an aqueous reaction medium by the process according to the invention.

The process according to the invention has a number of advantages. Carrying out the reaction steps in a one-pot process simplifies the process and thereby enables preparation costs to be reduced. Furthermore, the starting substances, that is to say 1-chloro-2-aryloxy-1-alkenes (II), can easily be prepared from inexpensive raw materials which are readily available on an industrial scale, such as isobutene, 2-methyl-2-butene and isoprene (German Patent Application No. P 30 49 461.2 of 30.12.1980 (Le A 20 764)). Unsaturated 1-aryloxymethyl ketones which are not available by the known chlorination of corresponding methyl ketones can also be synthesized by the process according to the invention.

If, for example, 1-chloro-2-(4-chlorophenoxy)-3,3-dimethyl-1-butene is used as the starting substance, the course of the reaction can be represented by the following equation:

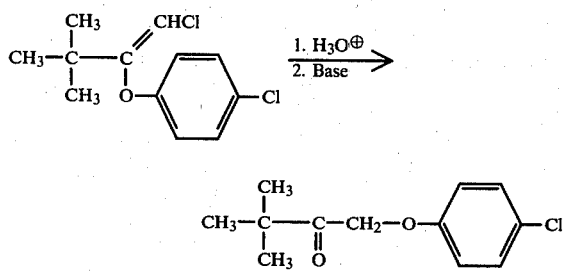

The general formula (II) provides a definition of the 1-halogeno-2-aryloxy-1-alkenes to be used as starting substances. Preferably, in this formula,
$R^1$ and $R^2$, which can be identical or different, each represent alkyl, alkenyl or alkyny with in each case up to 4 carbon atoms, or phenyl, the alkyl and phenyl groups optionally being substituted by halogen, nitro, phenyl, halogenophenyl, alkoxy with up to 3 carbon atoms, phenoxy or halogenophenoxy, or
$R^1$ and $R^2$ together form an alkylene chain with 2 to 7 carbon atoms,
$R^3$ represents alkyl with up to 10 (especially up to 6) carbon atoms or aryl with 6 to 10 carbon atoms (especially phenyl), the alkyl or aryl radicals optionally being substituted by halogen, nitro, phenyl, halogenophenyl, alkoxy with up to 3 carbon atoms, phenoxy or halogenophenoxy,
$R^4$ represents chlorine, fluorine, alkyl or alkoxy with in either case up to 3 carbon atoms, phenyl or halogenophenyl, and
n represents 0, 1 or 2.
Hal preferably represents chlorine.

Specific examples which may be mentioned of the 1-halogeno-2-aryloxy-1-alkenes of the formula (II) to be used according to the invention are: 1-chloro-2-phenoxy-3,3-dimethyl-1-butene, 1-chloro-2-(4-chlorophenoxy)-3,3-dimethyl-1-butene, 1-chloro-2-(2,4-dichlorophenoxy)-3,3-dimethyl-1-butene, 1-chloro-2-(2,4,6-trichlorophenoxy)-3,3-dimethyl-1-butene, 1-chloro-2-(4-fluorophenoxy)-3,3-dimethyl-1-butene, 1-chloro-2-(2-chlorophenoxy)-3,3-dimethyl-1-butene, 1-chloro-2-(2-fluorophenoxy)-3,3-dimethyl-1-butene, 1-chloro-2-(2-chloro-4-fluorophenoxy)-3,3-dimethyl-1-butene, 1-chloro-2-(2-methyl-4-chlorophenoxy)-3,3-dimethyl-1-butene, 1-chloro-2-(4-(p-chlorophenyl)- phenoxy)-3,3-dimethyl-1-butene, 1-chloro-2-phenoxy-3,3-dimethyl-1-pentene, 1-chloro-2-(4-chlorophenoxy)-3,3-dimethyl-1-pentene, 1-chloro-2-(4-fluorophenoxy)-3,3-dimethyl-1-pentene, 1-chloro-2-(2,4-dichlorophenoxy)-3,3-dimethyl-1-pentene, 1-chloro-2-phenoxy-3,3-dimethyl-1,4-pentadiene, 1-chloro-2-(4-chlorophenoxy)-3,3-dimethyl-1,4-pentadiene, 1-chloro-2-(4-fluorophenoxy)-3,3-dimethyl-1,4-pentadiene, 1-chloro-2-(2,4-dichlorophenoxy)-3,3-dimethyl-1,4-pentadiene, 1-chloro-2-phenoxy-3,3-dimethyl-5-fluoro-1-pentene, 1-chloro-2-(4-chlorophenoxy)-3,3-dimethyl-5-fluoro-1-pentene, 1-chloro-2-(2,4-dichlorophenoxy)-3,3-dimethyl-5-fluoro-1-pentene, 1-chloro-2-phenoxy-3,3-diethyl-1-pentene, 1-chloro-2-(4-chlorophenoxy)-3,3-diethyl-1-pentene, 1-chloro-2-(4-fluorophenoxy)-3,3-diethyl-1-pentene, 1-chloro-2-(2,4-dichlorophenoxy)-3,3-diethyl-1-pentene, 1-chloro-2-phenoxy-3-methyl-1-butene, 1-chloro-2-(chlorophenoxy)-3-methyl-1-butene, 1-chloro-2-(4-fluorophenoxy)-3-methyl-1-butene, 1-chloro-2-(2,4-dichlorophenoxy)-3-methyl-1-butene, 1-chloro-2-(4-chlorophenoxy)-3,3,4-trimethyl-1-pentene, 1-chloro-2-(4-chlorophenoxy)-3,3,5,5-tetramethyl-1-hexene, 1-chloro-2-(4-chlorophenoxy)-3,3-dimethyl-1-octene, 1-chloro-2-(4-chlorophenoxy)-3-methyl-3-(4-chlorophenyl)-1-butene, 1-chloro-2-(4-chlorophenoxy)-3-methyl-3-(2,4-dichlorophenyl)-1-butene, 1-chloro-2-(4-chlorophenoxy)-3,3-dimethyl-pent-1-en-4-yne, 1-chloro-2,5-di-(4-chlorophenoxy)-3,3-dimethyl-1-pentene, 1-chloro-2,5-di-(2,4-dichlorophenoxy)-3,3-dimethyl-1-penten, 1-(2-chloro-1-[4-chlorophenoxy]-vinyl)-1-methyl-cyclohexane, 1-(2-chloro-1-[4-chlorophenoxy]-vinyl)-1-ethyl-cyclopentane and 1-(2-chloro-1-[4-chlorophenoxy]-vinyl)-1-methyl-cyclopropane.

The 1-halogeno-2-aryloxy-1-alkenes mentioned can be obtained in a simple manner from olefins by adding on hydrogen halide, subsequently adding on a vinylidene halide in the presence of acid catalysts (for example aluminium chloride) and reacting the resulting adduct with alkali metal phenolates (German Patent Application No. P 30 29 270.7 of 1.8.1980 [Le A 20 475] and P 30 49 461.2 of 30.12.1980 [Le A 20 764]).

Possible diluents for the process according to the invention are organic solvents which are inert towards the reactants. It is preferred to use polar solvents, such as alcohols, for example methanol, ethanol or ethylene glycol; and ethers, such as tetrahydrofuran or dioxane; ketones, such as acetone or methyl ethyl ketone; or acetonitrile, dimethylformamide, dimethylsulphoxide or N-methylpyrrolidone. Mixtures or solutions consisting of one or more organic solvents (for example alcohols or ketones) and water can also be used. It is also possible to use a two-phase system (organic solvent/water) with customary phase-transfer catalysts (for example ammonium or phosphonium salts).

The hydrolysis is carried out with an acid, such as hydrochloric acid, formic acid, acetic acid, trifluoroacetic acid, oxalic acid, sulphuric acid, methanesulphonic acid or p-toluenesulphonic acid; the acids can be present in aqueous dilution. Hydrochloric acid is preferably used. The hydrolysis is carried out in the temperature range between +20° and 150° C., preferably between 40° and 100° C., until it is about 95 to 100% complete.

Possible basic substances required for the reaction according to the invention are both inorganic and organic bases. It is preferred to use an alkali metal carbonate or alkaline earth metal carbonate, for example sodium carbonate, potassium carbonate or calcium carbonate; an alkali metal hydroxide or alkaline earth metal hydroxide, for example sodium hydroxide, potassium hydroxide, calcium hydroxide or magnesium hydroxide; an alkali metal bicarbonate for example sodium bicarbonate; an alkaline earth metal oxide, for example calcium oxide; or an amine, such as triethylamine.

After the basic substance has been added, the reaction is brought to completion at a temperature between +20° and 150° C., preferably at from 40° to 100° C. This can be carried out either under normal pressure in an open system or under pressure in an autoclave.

For carrying out the acid hydrolysis, an equimoler amount of a monobasic acid is preferably employed per mol of 1-halogeno-2-aryloxy-1-alkene of the formula (II). After the hydrolysis, the reaction mixture is rendered weakly alkaline by addition of, preferably, 2 mols of an alkali metal carbonate, for example sodium carbonate or potassium carbonate. Working up is effected by adding a water-immiscible solvent and washing the reaction mixture with water, drying the organic phase and stripping off the diluent. If necessary, the resulting product of the formula (I) can be purified by distillation. The reaction is in general carried out as a one-pot process, although it can also be carried out in two separate stages.

The 1-aryloxy-methyl ketones of the formula I which are producible by the process according to the invention are suitable as intermediate products for the preparation of fungicidally active azole derivatives. They can be converted into 1-halogeno-1-aryloxy-methyl ketones by halogenation, and these ketones can then be reacted with imidazole or 1,2,4-triazole. The reaction with, for example, triazoles leads to compounds which have a high activity against phytopathogenic fungi (in this context, see DE-AS (German Published Specification) No. 2,201,063 or the corresponding U.S. Pat. No. 3,912,752).

The examples which follow illustrate the process according to the invention.

PREPARATIVE EXAMPLES

Example 1

(a) 1,3-Dichloro-3-methyl-butane was reacted with 1,1-dichloroethene in the presence of aluminum chloride in the temperature range between −10° and +5° C. 3,3-Dimethyl-1,1,5-trichloro-1-pentene was thereby obtained and was purified by distillation. 1,1-Dichloro-3,3-dimethyl-1,4-pentadiene was obtained by splitting off hydrogen chloride with quinoline in the temperature range between 200° and 240° C. (See Application Ser. No. 281,614 filed July 9, 1981 now pending, corresponding to German Patent Application No. P 30 29 270.7 of 1.8.1980).

(b) 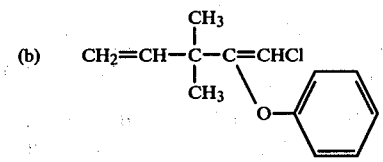

116 g (1 mol) of sodium phenolate and 82.5 g (0.5 mol) of 1,1-dichloro-3,3-dimethyl-1,4-pentadiene were heated under reflux in 500 ml of dimethylformamide for 18 hours. The solution was diluted with methylene chloride and extracted by shaking with dilute sodium hydroxide solution. After the organic phase had been dried over sodium sulphate, the solvent was stripped off in vacuo. 108.5 g of crude product remained, and were distilled. 93.6 g of 1-chloro-3,3-dimethyl-2-phenoxy-1,4-pentadiene pass over at boiling point 80°–90° C./0.5 mm Hg. The pure yield was 84% of theory. NMR (CDCl₃): δ1.25 (s, 6H), 4.9–6.2 (—CH=CH₂), 5.85 (s, 1H) and 6.8–7.4 (m, 5H).

(c) 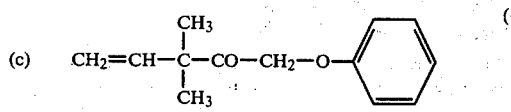 (1)

22.2 g (0.1 mol) of 1-chloro-2-phenoxy-3,3-dimethyl-1,4-pentadiene were heated under reflux in a mixture of 10 ml of acetone and 10 ml of concentrated hydrochloric acid for 3 hours. 27.6 g (0.2 mol) of potassium carbonate were then added and the mixture was diluted with a further 65 ml of acetone and heated under reflux for 19 hours. The solution was diluted with methylene chloride and extracted several times by shaking with water. After the mixture had been dried over sodium sulphate, the solvent was stripped off and 20.1 g of crude product were obtained. Distillation at boiling point 80°–83° C./0.5 mm Hg gave 16.9 g of 1-phenoxy-3,3-dimethyl-pent-4-en-2-one. The yield was 83% of theory. δ NMR (CDCl₃): 1.3 (s,6H), 4.8 (s,2H), 5.0–6.2 (m, —CH=CH₂) and 6.7–7.4 (m, 5H).

Example 2

(a) 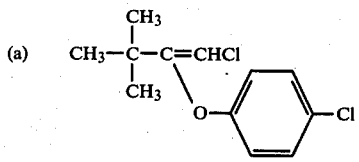

26 g (0.2 mol) of p-chlorophenol were reacted with 40 ml of 30% strength sodium methylate solution (0.2 mol) in 150 ml of dimethylformamide. After the methanol had been stripped off, a further 50 ml of dimethylformamide were distilled off under 20 mbar. 15.3 g (0.1 mol) of 1,1-dichloro-3,3-dimethyl-1-butene were then added and the mixture was heated under reflux for 18 hours. The solution was diluted with methylene chloride and extracted three times by shaking with dilute sodium hydroxide solution. The organic phase was dried over sodium sulphate and the solvent was removed in vacuo. Distillation gave dimethylformamide in the first runnings, and 20 g of 1-chloro-3,3-dimethyl-2-(4'-chlorophenoxy)-1-butene, that is to say 81% of theory, as the main fraction at boiling point 110°–128° C./0.15 mm Hg. NMR (CDCl₃): δ 1.15 (s, 9H), 5.9 (s, 1H) and 6.8–7.4 (m, 4H).

(b) 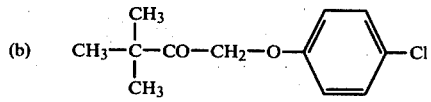 (2)

12.25 g (0.05 mol) of 1-chloro-3,3-dimethyl-2-(4'-chlorophenoxy)-1-butene were heated under reflux in 10 ml of acetone and 5 ml of concentrated hydrochloric acid for 7 hours. 13.8 g (0.1 mol) of potassium carbonate and 30 ml of acetone were then added and the mixture was heated under reflux for a further 7.5 hours. The suspension was diluted with methylene chloride and extracted several times by shaking with water. After the mixture had been dried over sodium sulphate and the solvent had been removed, 11.34 g of crude product were obtained and were distilled at boiling point 108°–128° C./0.15 mm Hg; the product was then solidified. 10.2 g of 1-(4'-chlorophenoxy)-3,3-dimethyl-butan-2-one of melting point 58°–60° C. were obtained, that is to say 90% of theory. NMR (CDCl₃): δ 1.2 (s, 9H), 4.85 (s, 2H) and 6.7–7.3 (m, 4H).

It will be appreciated that the instant specification and examples are set forth by way of illustration and not limitation, and that various modifications and changes may be made without departing from the spirit and scope of the present invention.

We claim:

1. A process for the preparation of a 1-aryloxymethyl ketone of the formula

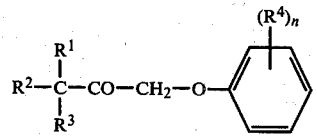

in which
R¹ and R² each independently is alkyl, alkenyl or alkynyl with up to 4 carbon atoms, or phenyl, the alkyl and phenyl groups optionally being substituted by halogen, nitro, phenyl, halogenophenyl, alkoxy with up to 3 carbon atoms, phenoxy or halogenophenoxy, or
R¹ and R² together form an alkylene chain with 2 to 7 carbon atoms,
R³ is alkyl with up to 10 carbon atoms or aryl with 6 to 10 carbon atoms, the alkyl or aryl radicals optionally being substituted by halogen, nitro, phenyl, halogenophenyl, alkoxy with up to 3 carbon atoms, phenoxy or halogenophenoxy,
R⁴ each independently is halogen, alkyl, alkoxy, nitro, alkyl or alkoxy with up to 3 carbon atoms, phenyl or halogenophenyl, and
n is 0, 1, 2 or 3,
comprising contacting a 1-halogeno-2-aryloxy-1-alkene of the formula

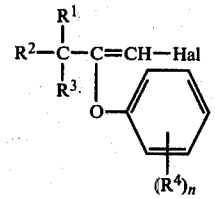

in which Hal is chlorine or bromine,
with acid at a temperature from about 20° to 150° C., until about 95 to 100% of the alkene reacts, adding a base, and then allowing the reaction to go to completion under weakly alkaline conditions by continuing contact of the reactants at about 20° to 150° C.

2. A process according to claim 1, wherein all stages of the reaction are effected in a single vessel.

3. A process according to claim 1, wherein the acid reaction and the subsequent alkaline reaction are each carried out in the temperature range of about 40° to 100° C.

4. A process according to claim 1, wherein the acid reaction is effected in the presence of hydrochloric acid, sulphuric acid, formic acid, acetic acid, trifluoro-acetic acid, methanesulphonic acid or p-toluenesulphonic acid.

5. A process according to claim 1, wherein the basic substance is an alkali metal carbonate, alkaline earth metal carbonate, alkali metal hydroxide, alkaline earth metal hydroxide, alkali metal bicarbonate, alkaline earth metal oxide or amine.

6. A process according to claim 1, wherein the acid reaction is effected in the presence of an inert organic solvent in admixture with water as a solution or as a two-phase system.

7. A process according to claim 1, wherein about 1 mol of monobasic acid and 2 mols of alkali metal carbonate are employed per mol of the 1-halogeno-2-aryloxy-1-alkene.

8. A process according to claim 1, in which n is 0, 1 or 2.

9. A process according to claim 1, in which Hal is chlorine.

10. A process according to claim 9, wherein all stages of the reaction are effected in a single vessel at a temperature from about 40° to 100° C. and in the presence of an inert organic solvent, optionally in admixture with water as a solution or as a two-phase system, about 1 mol of a monobasic acid and 2 mols of alkali metal carbonate being employed per mol of the 1-halogeno-2-aryloxy-1-alkene.

* * * * *